United States Patent

Barrus

(10) Patent No.: US 9,962,191 B2
(45) Date of Patent: May 8, 2018

(54) SPINAL IMPLANT AND METHODS OF USE THEREOF

(71) Applicant: K2M, Inc., Leesburg, VA (US)

(72) Inventor: Michael Barrus, Ashburn, VA (US)

(73) Assignee: K2M, Inc., Leesburg, VA (US)

( * ) Notice: Subject to any disclaimer, the term of this patent is extended or adjusted under 35 U.S.C. 154(b) by 0 days. days.

(21) Appl. No.: 15/410,118

(22) Filed: Jan. 19, 2017

(65) Prior Publication Data

US 2017/0202581 A1    Jul. 20, 2017

Related U.S. Application Data

(60) Provisional application No. 62/280,199, filed on Jan. 19, 2016.

(51) Int. Cl.
*A61B 17/70*    (2006.01)
*A61B 17/86*    (2006.01)

(52) U.S. Cl.
CPC ...... *A61B 17/7034* (2013.01); *A61B 17/7035* (2013.01); *A61B 17/8685* (2013.01)

(58) Field of Classification Search
CPC ................. A61B 17/7034; A61B 17/7037
USPC ......................................................... 606/269
See application file for complete search history.

(56) References Cited

U.S. PATENT DOCUMENTS

| | | | |
|---|---|---|---|
| 5,125,839 A * | 6/1992 | Ingber ............... | A61C 8/0001 433/169 |
| 5,443,467 A | 8/1995 | Biedermann et al. | |
| 5,554,157 A * | 9/1996 | Errico ............... | A61B 17/7037 606/264 |
| 5,647,873 A * | 7/1997 | Errico ............... | A61B 17/7037 606/264 |
| 5,733,286 A * | 3/1998 | Errico ............... | A61B 17/7037 606/266 |
| 5,885,286 A | 3/1999 | Sherman et al. | |
| 5,891,145 A | 4/1999 | Morrison et al. | |
| 6,471,705 B1 | 10/2002 | Biedermann et al. | |
| 6,554,834 B1 | 4/2003 | Crozet et al. | |
| 6,716,214 B1 | 4/2004 | Jackson | |
| 6,723,100 B2 | 4/2004 | Biedermann et al. | |
| 7,250,052 B2 | 7/2007 | Landry et al. | |
| 7,479,156 B2 | 1/2009 | Lourdel et al. | |
| 7,766,945 B2 | 8/2010 | Nilsson et al. | |
| 7,842,073 B2 | 11/2010 | Richelsoph et al. | |
| 7,862,594 B2 | 1/2011 | Abdelgany | |

(Continued)

*Primary Examiner* — Ellen C Hammond
*Assistant Examiner* — Stuart S Bray
(74) *Attorney, Agent, or Firm* — Carter, DeLuca, Farrell & Schmidt, LLP

(57) ABSTRACT

A spinal fixation device includes a housing defining a longitudinal axis, a bone screw member, a locking ring, and a crush ring. The bone screw member includes a head that is selectively securable within the housing and a threaded shaft. The locking ring is disposed within the housing and is radially expandable to a partially expanded position when the head of the bone screw member is positioned therein to retain the head within the housing. The crush ring is disposed within the housing proximal to the locking ring and adjacent the head of the bone screw member. The crush ring pushes against the head of the bone screw member when it transitions from an initial state to a deformed state when a force is applied thereto, which expands the locking ring to a fully expanded position to fix the bone screw member to the housing.

17 Claims, 4 Drawing Sheets

(56) References Cited

U.S. PATENT DOCUMENTS

| | | |
|---|---|---|
| 7,922,748 B2 | 4/2011 | Hoffman |
| 7,955,363 B2 * | 6/2011 | Richelsoph ........ A61B 17/7037 |
| | | 600/246 |
| 8,308,729 B2 | 11/2012 | Nunley et al. |
| 8,409,255 B2 | 4/2013 | Richelsoph |
| 8,696,718 B2 | 4/2014 | Barrus et al. |
| 8,945,194 B2 | 2/2015 | Biedermann et al. |
| 8,961,523 B2 | 2/2015 | Barrus et al. |
| 9,421,041 B2 | 8/2016 | Richelsoph |
| 9,566,093 B2 | 2/2017 | Biedermann et al. |
| 9,603,629 B2 | 3/2017 | Richelsoph |
| 9,730,742 B2 * | 8/2017 | Lewis ................ A61B 17/8047 |
| 2005/0154391 A1 | 7/2005 | Doherty et al. |
| 2006/0247631 A1 | 11/2006 | Ahn et al. |
| 2008/0086131 A1 * | 4/2008 | Daly .................. A61B 17/7032 |
| | | 606/264 |
| 2009/0318978 A1 * | 12/2009 | Podgorski .......... A61B 17/7059 |
| | | 606/290 |
| 2010/0145460 A1 * | 6/2010 | McDonough ...... A61B 17/1728 |
| | | 623/17.16 |
| 2011/0152947 A1 * | 6/2011 | Kirschman ........ A61B 17/7032 |
| | | 606/302 |
| 2012/0116463 A1 * | 5/2012 | Razian ............... A61B 17/7032 |
| | | 606/305 |
| 2012/0303069 A1 * | 11/2012 | Lin .................... A61B 17/8047 |
| | | 606/290 |
| 2013/0023939 A1 * | 1/2013 | Pischl ................ A61B 17/8047 |
| | | 606/286 |
| 2014/0222086 A1 * | 8/2014 | Kuster ............... A61B 17/7059 |
| | | 606/290 |
| 2016/0106473 A1 * | 4/2016 | Rezach ............. A61B 17/7035 |
| | | 606/265 |
| 2017/0340362 A1 * | 11/2017 | Jackson ............. A61B 17/7037 |

* cited by examiner

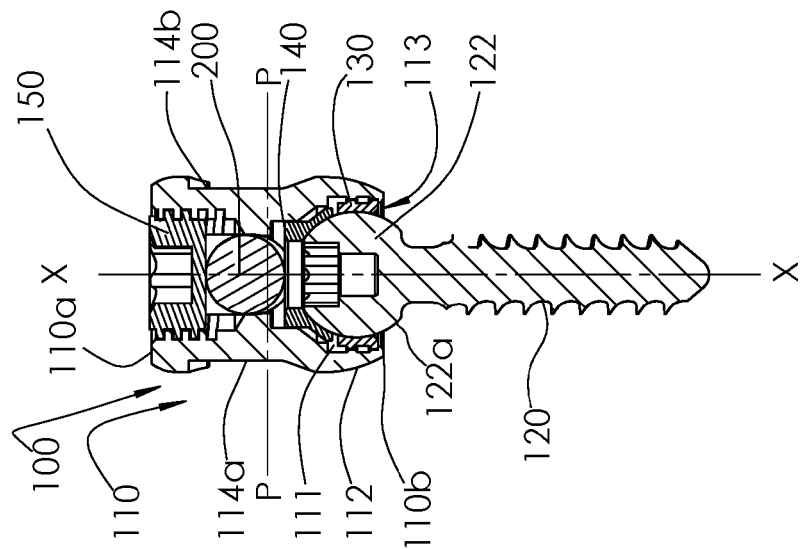
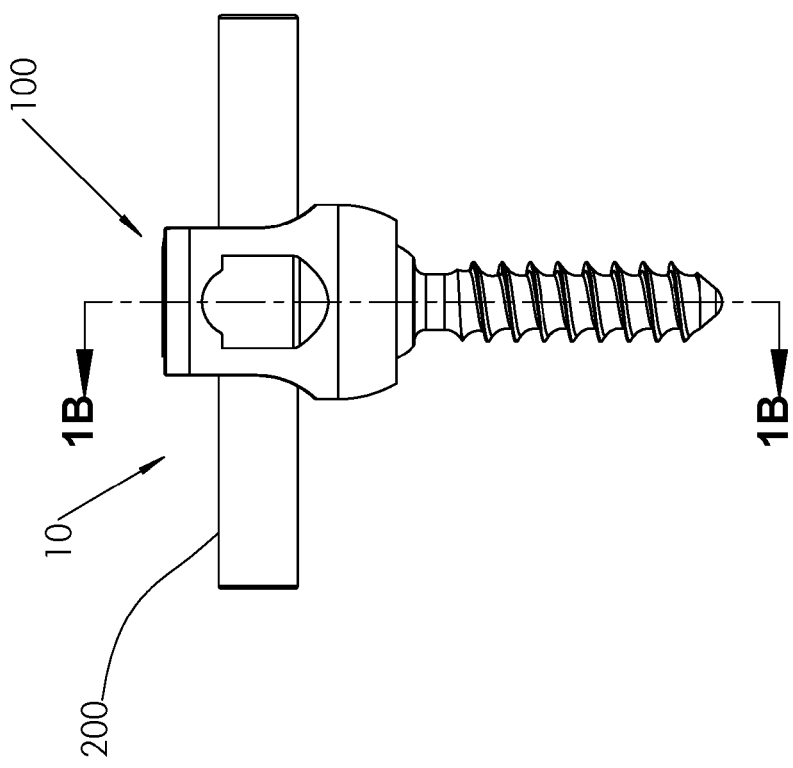
FIG. 1B
FIG. 1A

SPINAL IMPLANT AND METHODS OF USE THEREOF

CROSS-REFERENCE TO RELATED APPLICATIONS

This application claims the benefit of, and priority to, U.S. Provisional Patent Application Ser. No. 62/280,199, which was filed on Jan. 19, 2016, the entire contents of which are hereby incorporated herein by reference.

TECHNICAL FIELD

The present disclosure relates generally to a spinal fixation device, and more particularly, to a spinal implant and methods for securing a spinal fixation device during orthopedic spine surgery.

BACKGROUND

The spinal column is a complex system of bones and connective tissues that provide support for the human body and protection for the spinal cord and nerves. The adult spine includes an upper portion and a lower portion. The upper portion has twenty-four discrete bones, which are subdivided into three areas including seven cervical vertebrae, twelve thoracic vertebrae, and five lumbar vertebrae. The lower portion has the sacral and coccygeal bones. The cylindrical shaped bones, called vertebral bodies, progressively increase in size from the upper portion downwards to the lower portion.

An intervertebral disc along with two posterior facet joints cushion and dampen the various translational and rotational forces exerted upon the spinal column. The intervertebral disc is a spacer located between two vertebral bodies. The facets provide stability to the posterior portion of adjacent vertebrae. The spinal cord is housed in the canal of the vertebral bodies. It is protected posteriorly by the lamina. The lamina is a curved surface with three main protrusions. Two transverse processes extend laterally from the lamina, while the spinous process extends caudally and posteriorly. The vertebral bodies and lamina are connected by a bone bridge called the pedicle.

The spine is a flexible structure capable of a large range of motion. There are various disorders, diseases, and types of injury, which restrict the range of motion of the spine or interfere with important elements of the nervous system. The problems include, but are not limited to, scoliosis, kyphosis, excessive lordosis, spondylolisthesis, slipped or ruptured disc, degenerative disc disease, vertebral body fracture, and tumors. Persons suffering from any of the above conditions typically experience extreme and/or debilitating pain, and often times diminished nerve function. These conditions and their treatments can be further complicated if the patient is suffering from osteoporosis, or bone tissue thinning and loss of bone density.

There are many known spinal conditions, e.g., scoliosis, that require the imposition and/or maintenance of corrective forces on the spine in order to return the spine to its normal condition. As a result, numerous devices (e.g., alignment systems) have been developed for use in spinal fixation. One type of spinal construct may include, for example, one or more spinal rods that can be placed parallel to the spine with spinal fixation devices (such as hooks, screws, or plates) interconnected between the spinal rods at selected portions of the spine. The spinal rods can be connected to each other via cross-connecting members to provide a more rigid support and alignment system.

When a spinal rod is used as a support and stabilizing member, commonly, a series of two or more screws are inserted into two or more vertebrae to be instrumented. A spinal rod is then placed within or coupled to the heads of the screws, or is placed within a connecting device that links the spinal rod and the heads of the screws, and the connections are tightened. In this way, a rigid supporting structure is fixed to the vertebrae, with the spinal rod providing the support that maintains and/or promotes correction of the vertebral malformation or injury.

Some spinal fixation devices allow one or more degrees of freedom between a fastening portion and a receiving portion of the spinal fixation device, thereby reducing the required precision of placement of the spinal fixation device. The receiving portion of the spinal fixation device may be multi-axially or polyaxially positionable. The receiving portion can be positioned so as to easily receive a spinal rod, limiting or removing much of the positioning difficulty inherent in prior devices. However, such devices provide a maximum angle on the order of 45 degrees between the receiving portion of the spinal fixation device with respect to a longitudinal axis of the fastening portion of the spinal fixation device.

The surgeon attaches the spinal fixation devices to the spine in the appropriate anatomical positions then attaches the spinal rod to the spinal fixation devices. In conjunction, the surgeon manipulates the spinal column and/or individual vertebra to provide the desired treatment for the spinal defect. Subsequently, the spinal rod and fixation devices are locked in a desired arrangement.

While the aforementioned spinal fixation devices are suitable for the above uses, a need exists for a spinal fixation device that can provide a larger degree of angulation between a receiving portion of the spinal fixation device with respect to a longitudinal axis of the fastening portion of the spinal fixation device to facilitate the manipulation of the spine and reduction of various spinal deformities, especially those related to scoliosis.

SUMMARY

The present disclosure is directed to a spinal fixation device having a large degree of angulation of a bone screw member with respect to a housing of the spinal fixation device (i.e., up to about 95°) to maintain the bone screw member in a bone structure and to allow the housing to be sufficiently adjusted to capture a spinal rod and lock it into place with the insertion of a set screw into the housing. The spinal fixation device is advantageous in surgical procedures requiring a large correction of the spine.

In accordance with an aspect of the present disclosure, a spinal fixation device includes a housing defining a longitudinal axis, a bone screw member, a locking ring, and a crush ring. The bone screw member includes a head that is selectively securable within the housing and a threaded shaft. The locking ring is disposed within the housing and biased in a neutral position. The locking ring is radially expandable to a partially expanded position when the head of the bone screw member is positioned therein, and the partially expanded position retains the head of the bone screw member within the housing. The crush ring is disposed within the housing proximal to the locking ring and adjacent the head of the bone screw member. The crush ring has an initial state and a deformed state when a force is applied thereto. The crush ring pushes against the head of the bone screw member when it transitions from the initial state to the deformed state which expands the locking ring to a fully expanded position to fix the bone screw member to the housing.

The bone screw member may have a cone of angulation of about 95° relative to the longitudinal axis of the housing.

In embodiments, the housing includes a body portion and opposing walls extending proximally from the body portion. The housing is divided by a plane that is substantially equidistant from proximal and distal ends of the housing and substantially perpendicular to the longitudinal axis of the housing.

The head of the bone screw member may be disposed within the body portion of the housing distal to the plane. The crush ring may be disposed within the body portion of the housing distal to the plane. In some embodiments, the housing includes a channel defined between the opposing walls thereof, and a proximal end of the crush ring is disposed adjacent to the channel of the housing.

In embodiments, the body portion of the housing has an inner surface including relief features defined therein having an outer diameter that is larger than an outer diameter of the locking ring. The locking ring may include engagement features configured to engage the relief features of the housing when expanded, and/or notches extending longitudinally through portions thereof in spaced relation relative to each other.

The crush ring may include a body portion having a flange disposed radially therearound, the flange configured to contact the head of the bone screw member when the head is disposed within the housing.

In embodiments, a spinal rod is selectively securable to the housing of the spinal fixation device. In some embodiments, the spinal rod is positionable within a channel of the housing, and the crush ring is movable to the deformed state and the locking ring is expandable to the fully expanded position when the spinal rod is fully reduced into the channel.

In accordance with another aspect of the present disclosure, a method of aligning vertebral bodies of a spine includes fastening a bone screw member of a spinal fixation device to a vertebral body, and positioning a portion of a spinal rod within a channel defined in a housing of the spinal fixation device. The spinal fixation device includes a housing extending along a longitudinal axis, a bone screw member, a locking ring, and a crush ring. The bone screw member includes a head that is selectively securable within the housing and a threaded shaft. The locking ring is disposed within the housing and biased in a neutral position. The locking ring is radially expandable to a partially expanded position when the head of the bone screw member is positioned therein, and the partially expanded position retains the head of the bone screw member within the housing. The crush ring is disposed within the housing proximal to the locking ring and adjacent the head of the bone screw member. The crush ring has an initial state and a deformed state when a force is applied thereto. The crush ring pushes against the head of the bone screw member when transitioning from the initial state to the deformed state which expands the locking ring to a fully expanded position to fix the bone screw member to the housing.

The method may include rotating the housing with respect to the bone screw member, and fully reducing the spinal rod into the channel. In embodiments, rotating the housing includes moving the housing within a cone of angulation of about 95° of the bone screw member relative to the longitudinal axis of the housing.

The method may include assembling the spinal fixation device prior to fastening the bone screw member to the vertebral body. In embodiments, assembling the spinal fixation device includes: positioning the crush ring within the housing; positioning the locking ring in the housing; and inserting the head of the bone screw member into the housing and through the locking ring to couple the bone screw member to the housing.

Other aspects, features, and advantages will be apparent from the description, drawings, and the claims.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure, wherein:

FIG. 1A is a side view of a spinal fixation system including a spinal fixation device in a straight position and a spinal rod in accordance with an embodiment of the present disclosure, the spinal fixation system shown in a locked position;

FIG. 1B is a cross-sectional view of the spinal fixation system of FIG. 1A, taken along line 1B-1B of FIG. 1A;

DETAILED DESCRIPTION

Figure 2B:
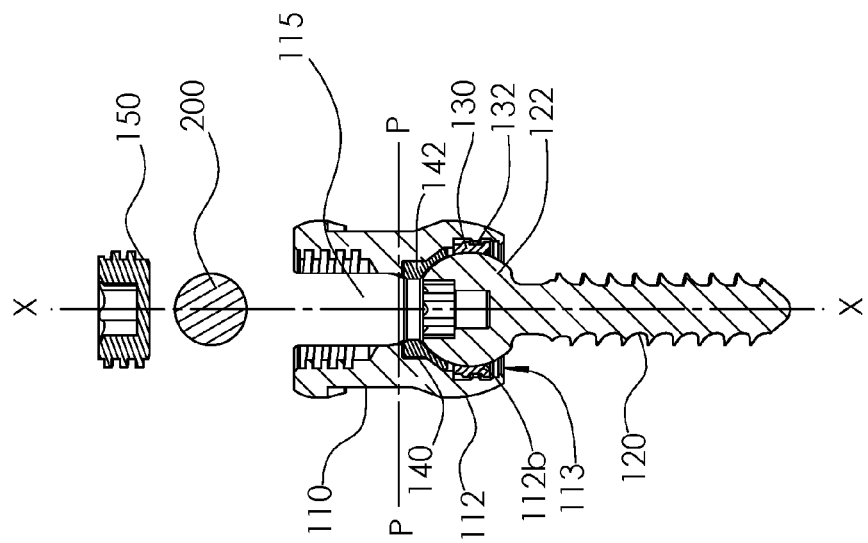
FIG. 2B is a cross-sectional view of the spinal fixation system of FIGS. 1A and 1B, taken along line 2B-2B of FIG. 2A.

Embodiments of the present disclosure are now described in detail with reference to the drawings in which like reference numerals designate identical or corresponding elements in each of the several views. As used herein, the term "clinician" refers to a doctor, nurse, or other care provider and may include support personnel. Throughout this description, the term "proximal" refers to a portion of a structure (e.g., a device or component thereof) closer to a clinician, while the term "distal" refers to a portion of the same structure further from the clinician. Additionally, in the drawings and in the description that follows, terms such as "front," "rear," "upper," "lower," "top," "bottom," and similar directional terms are used simply for convenience of description and are not intended to limit the disclosure. In the following description, well-known functions or constructions are not described in detail to avoid obscuring the present disclosure in unnecessary detail.

Figure 2A:
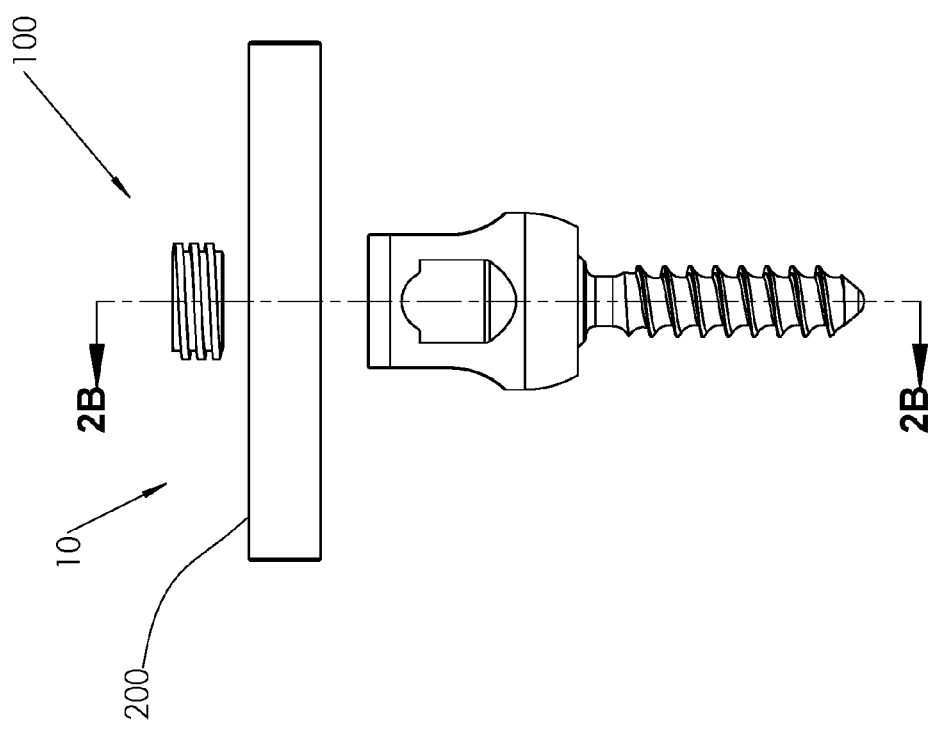
FIG. 2A is a side view of the spinal fixation system of FIG. 1A, shown in an unlocked position.

Referring now to FIGS. 1A and 2A, a spinal fixation system 10, including a spinal fixation device 100 and a spinal rod 200, is shown. The spinal fixation device 100 is in the form of a polyaxial pedicle (multi-planar) screw that is used to provide a point of fixation to a spine and attachment for the spinal rod 200. The spinal fixation device 100 provides a connection, via the spinal rod 200, between adjacent vertebrae which may not be in the same plane.

The spinal fixation device 100 is formed from biocompatible material(s) including, but not limited to, metals, such as stainless steel, cobalt chrome, titanium, and titanium alloy, as well as various polymers (e.g., polyether ether ketone (PEEK), polyphenylsulfone (PPSU), polyetherimide (PEI), polycarbonate (PC), polyethylene (PE), polypropylene (PP), polyacetal (POM), or other such engineering resin), or combinations of the aforementioned materials.

Figure 3:
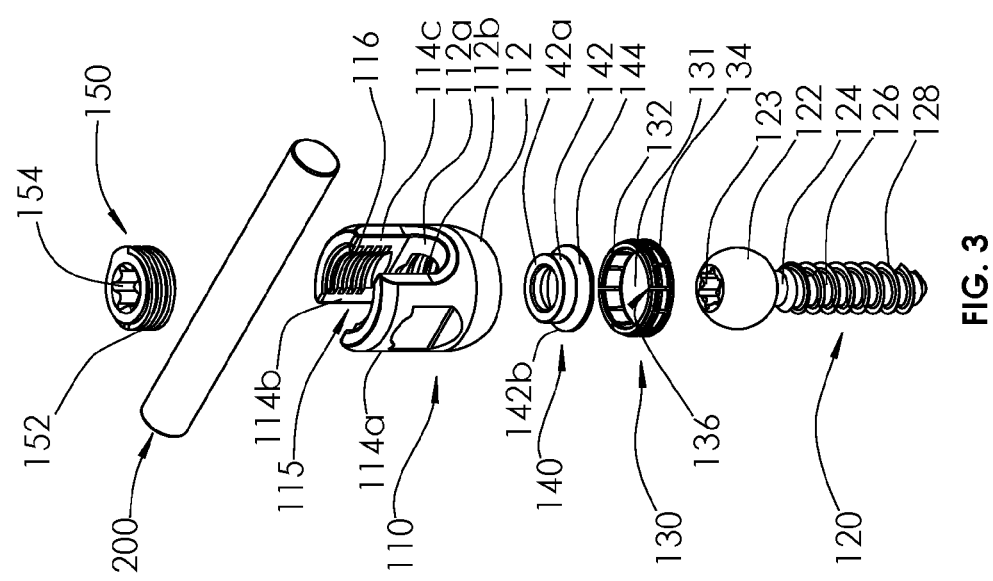
FIG. 3 is an exploded view of the spinal fixation system of FIGS. 1A-2B.
Figure 5:
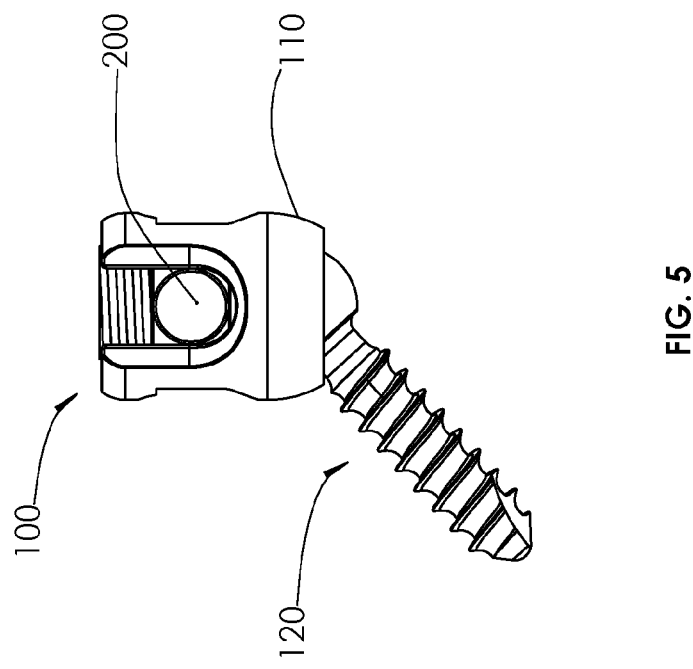
FIG. 5 is an end view of the spinal fixation system of FIGS. 1A-4, with the spinal fixation device in an angled position.
Figure 4:
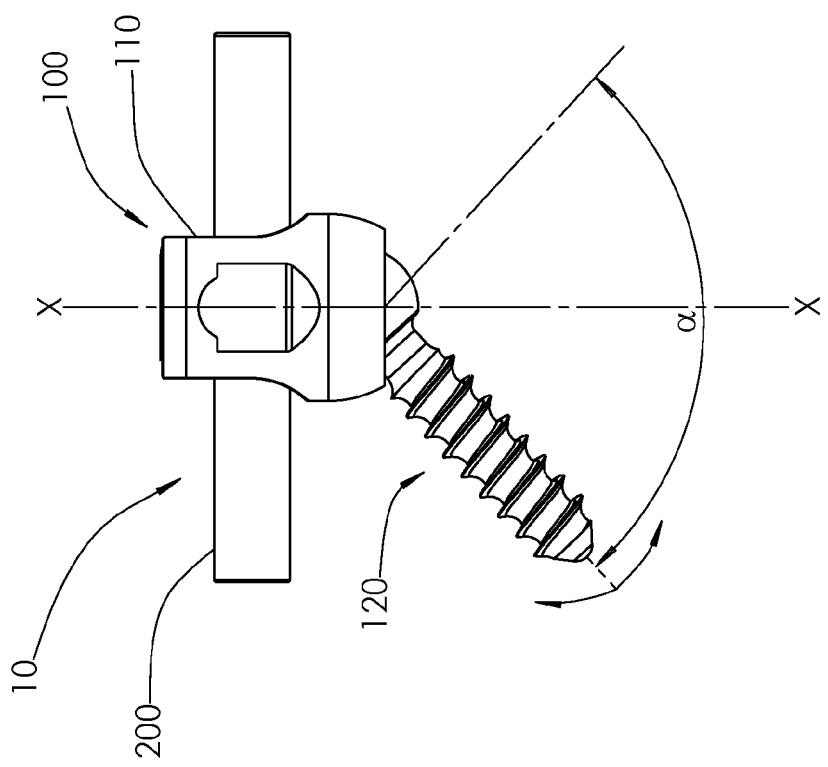
FIG. 4 is a side view of the spinal fixation system of FIGS. 1A-3, with the spinal fixation device in an angled position.

As shown in FIGS. 1B, 2B, and 3, the spinal fixation device 100 includes a housing 110, a bone screw member 120, a locking ring 130, a crush ring 140, and a set screw 150. The housing 110 extends along a longitudinal axis "X," and the bone screw member 120 also extends along the longitudinal axis "X" when the spinal fixation device 100 is in a straight or non-angled position. As shown in FIGS. 4 and 5, the bone screw member 120 of the spinal fixation device 100 is pivotable relative to the housing 110 at a cone angle, α, of up to about 95° from the longitudinal axis "X" of the housing 110 thereby providing a large degree of angulation of the bone screw member 120 relative to the housing 110 to accommodate various angled positions.

With continued reference to FIGS. 1B, 2B, and 3, the housing 110 of the spinal fixation device 100 includes a body portion 112 and opposing walls or arms 114a, 114b extending proximally therefrom, and defines an opening 111 therethrough that permits the reception of any suitable driving instrument (not shown) therethrough. The housing 110 is divided by a plane "P" that is substantially equidistant from proximal and distal ends 110a, 110b of the housing 110 (i.e., bisected) and substantially perpendicular to the longitudinal axis "X" of the housing 110.

The body portion 112 of the housing 110 is configured and dimensioned to accommodate a head 122 of the bone screw member 120, the locking ring 130, and the crush ring 140. The body portion 112 includes an inner surface 112a having a plurality of relief features 112b defined therein to aid in facilitating the securement of the locking ring 130 and the crush ring 140 to the bone screw member 120. The relief features 112b are in the form of a plurality of circumferential grooves having an outer diameter that is larger than the outer diameter of the locking ring 130 and the crush ring 140 to allow for the expansion thereof, as described in further detail below, without deformation of the housing 110 and potentially creating splay in opposing walls 114a, 114b.

As shown in FIG. 3, the opposing walls 114a, 114b of the housing 110 define a U-shaped saddle or channel 115 therebetween. Internal surfaces 114c of opposing walls 114a, 114b include threaded portions 116 that are threadably engageable with external threads 152 of the set screw 150 to facilitate the securement of the spinal rod 200 within the channel 115 of the housing 110 adjacent the crush ring 140 (see e.g., FIG. 1B).

With continued reference to FIG. 3, the bone screw member 120 includes, as viewed from proximal to distal, a head 122, a neck 124, and a shaft or shank 126 including threads 128 for engaging a bone structure (e.g., a vertebra). While the shaft 126 is shown as a screw, it should be understood that the shaft 126 may have other configurations for attachment to a bone structure, e.g., a pedicle hook, among other anchors within the purview of those skilled in the art. The head 122 of the bone screw member 120 includes a driving recess 123 defined in a proximal surface thereof. The driving recess 123 may be a hex feature, e.g., hexagonal or hexolobular in shape, or any other suitable configuration that is engageable with a suitable driving instrument (not shown) to enable the driving instrument to control the insertion and/or removal of the shaft 126 of the bone screw member 120 within the bone structure.

As shown in FIGS. 1B and 2B, the head 122 of the bone screw member 120 is substantially spherical in shape and selectively securable within the body portion 112 of the housing 110. The head 122, along with the locking ring 130 and the crush ring 140, are receivable within the housing 110 distal to the plane "P" such that a distal portion 122a of the head 122 extends distal to the distal end 110b of the housing 110. The head 122 of the bone screw member 120 is retained within the housing 110 via the locking ring 130, and axially and angularly fixed with respect to the housing 110 via deformation of the crush ring 140 and expansion of the locking ring 130, as described in further detail below.

With reference again to FIG. 3, the locking ring 130 has an annular body 132 defining a central opening 131 therethrough in which the head 122 of the bone screw member 120 is disposed when the bone screw member 120 is coupled to the housing 110. The locking ring 130 includes external engagement features 134 that are configured to engage the relief features 112b of the housing 110 when expanded, and notches 136 extending longitudinally through portions of the annular body 132 in spaced relation relative to each other which allow the locking ring 130 to expand radially outwardly to a partially expanded position (see e.g., FIG. 2B) and a fully expanded position (FIG. 1B), or compress radially inwardly to a compressed position (not shown) from its biased neutral position (FIG. 3).

The crush ring 140 includes a body portion 142 having a proximal end 142a that is configured to contact the spinal rod 200 when the spinal rod 200 is positioned within the channel 115 of the housing 110, and a distal end 142b including a flange 144 disposed therearound that is configured to contact the head 122 of the bone screw member 120 when the head 122 is disposed within the housing 110. The body portion 142 is a crushable region that is configured to engage the relief features 112b of the housing 110 when compressed from its initial state (see e.g., FIG. 2B) to a deformed state (FIG. 1B) by distal movement of the spinal rod 200 as it is fully reduced into the channel 115 of the housing 110.

The set screw 150 includes external threads 152 and a driving interface 154 that is engageable with any suitable driving instrument (not shown) to threadably engage the set screw 150 with the housing 110.

To assemble the housing 110 and the bone screw member 120 (e.g., from the disassembled configuration of FIG. 3 to the unlocked position of FIGS. 2A and 2B), the crush ring 140 is inserted into the housing 110 such that the proximal end 142a of the body portion 142 of the crush ring 140 is adjacent the channel 115 of the housing 110. The locking ring 130 is snapped into the housing 110 by radially compressing the annular body 132 of the locking ring 130 and inserting it into the housing 110 wherein the locking ring 130 expands or reverts back to its initial, unstressed configuration. The head 122 of the bone screw member 120 is then inserted into the body portion 112 of the housing 110 whereby, as the head 122 is passed through the central opening 131 (FIG. 3) of the locking ring 130, the relief features 112b of the housing 110 provides the annular body 132 of the locking ring 130 room to expand and snap onto the head 122 of the bone screw member 120 thereby coupling the bone screw member 120 to the housing 110. By employing the locking ring 130 to retain the head 122 of the bone screw member 120 within the housing 110, a bottom opening 113 of the housing 110 has a diameter greater than an outside diameter of the head 122 of the bone screw member 120 thereby allowing a greater range of angulation of the bone screw member 120 relative to the housing 110.

Once assembled, the bone screw member 120 is fastenable to a bone structure (e.g., a pedicle) and the housing 110 is repositionable in a plurality of orientations with respect to the bone screw member 120. The housing 110 is rotatable and pivotable about the head 122 of the bone screw member 120. A spinal rod 200 is then securable to the spinal fixation device 100 via the set screw 150.

To secure the spinal rod 200 to the spinal fixation device 100 (e.g., transitioning the spinal fixation device 100 from the unlocked position of FIGS. 2A and 2B, to the locked position of FIGS. 1A and 1B), the spinal rod 200 is positioned in the channel 115 of the housing 110 adjacent the proximal end 142a of the crush ring 140. The set screw 150 is then inserted into the housing 110, e.g., via threading engagement of the external threads 152 of the set screw 150 with the threaded portions 116 of opposing walls 114a, 114b of the housing 110. The set screw 150 is then rotated such that the set screw 150 contacts the spinal rod 200 and drives the spinal rod 200 which, in turn, drives the crush ring 140, distally towards the head 122 of the bone screw member 120. Once the desired angular position of the housing 110 with respect to the bone screw member 120 is reached, the set screw 150 is tightened further such that the spinal rod 200 crushes the crush ring 140 against the head 122 of the bone screw member 120 which, in turn, expands the locking ring 130 to the fully expanded position thereby fixing the angular relationship between the housing 110 and the bone screw member 120 and maintaining the spinal fixation device 100 in a fixed position.

In an embodiment of a method of use, a clinician performs a desired surgical procedure, such as a discectomy using an anterior approach. The clinician may then use instruments, such as rasps, curettes, among other various instruments, to prepare the endplate surfaces and a trial to size the vertebral space for an interbody device or a bone device, which the clinician places according to its surgical technique to fill the cleared disc space. It should be understood that the method of performing a discectomy may be by using any know procedures including, but not limited to, anterior lumbar interbody fusion (ALIF), transforaminal lumbar interbody fusion (TLIF), posterior lumbar interbody fusion (PLIF), or a lateral technique. It should also be understood that other surgical treatments and approaches may be used.

Next, using a posterior approach, spinal fixation devices 100 may be placed in the pedicles. A tap may be used to create a pathway in the pedicle through which the bone screw member 120 is inserted, or the bone screw member 120 may be a self-startertmy fastener or self-tapping fastener that creates the pathway in the pedicle without the use of a tap. Spinal rods 200 are then placed into the channels 115 of the housings 110 of the spinal fixation devices 100 and reduced into place utilizing methods or instruments within the purview of those skilled in the art including, but not limited to, rod reducers (not shown), such as those disclosed in commonly owned U.S. Pat. Nos. 8,308,729 and 8,961,523, the entire contents of each of which are hereby incorporated by reference herein. The set screws 150 are then inserted into the housings 110, as described above, to lock the spinal rods 200 in place.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown and described in connection with certain embodiments may be combined with the elements and features of certain other embodiments without departing from the scope of the present disclosure, and that such modifications and variation are also included within the scope of the present disclosure. Accordingly, the subject matter of the present disclosure is not limited by what has been particularly shown and described.

What is claimed is:

1. A spinal fixation device comprising:
a housing defining a longitudinal axis;
a bone screw member including a head and a threaded shaft, the head selectively securable within the housing;
a locking ring disposed within the housing, the locking ring biased in a neutral position and radially expandable to a partially expanded position when the head of the bone screw member is positioned therein, the partially expanded position retaining the head of the bone screw member within the housing; and
a crush ring disposed within the housing proximal to the locking ring and adjacent the head of the bone screw member, the crush ring having an initial state and a deformed state when a force is applied thereto, the crush ring pushing against the head of the bone screw member when transitioning from the initial state to the deformed state which expands the locking ring to a fully expanded position to fix the bone screw member to the housing.

2. The spinal fixation device of claim 1, wherein the bone screw member has a cone of angulation of about 95° relative to the longitudinal axis of the housing.

3. The spinal fixation device of claim 1, wherein the housing includes a body portion and opposing walls extending proximally from the body portion, the housing divided by a plane that is substantially equidistant from proximal and distal ends of the housing and substantially perpendicular to the longitudinal axis of the housing.

4. The spinal fixation device of claim 3, wherein the head of the bone screw member is disposed within the body portion of the housing distal to the plane.

5. The spinal fixation device of claim 3, wherein the crush ring is disposed within the body portion of the housing distal to the plane.

6. The spinal fixation device of claim 4, wherein the body portion of the housing has an inner surface including relief features defined therein having an outer diameter that is larger than an outer diameter of the locking ring.

7. The spinal fixation device of claim 6, wherein the locking ring includes engagement features configured to engage the relief features of the housing when the locking ring is expanded.

8. The spinal fixation device of claim 6, wherein the locking ring includes notches extending longitudinally through portions thereof in spaced relation relative to each other.

9. The spinal fixation device of claim 1, wherein the crush ring includes a body portion having a flange disposed radially therearound, the flange configured to contact the head of the bone screw member when the head is disposed within the housing.

10. The spinal fixation device of claim 3, wherein the housing includes a channel defined between the opposing walls thereof, and a proximal end of the crush ring is disposed adjacent to the channel of the housing.

11. The spinal fixation device of claim 1, wherein a spinal rod is selectively securable to the housing of the spinal fixation device.

12. The spinal fixation device of claim 11, wherein the spinal rod is positionable within a channel of the housing, the crush ring movable to the deformed state and the locking ring expandable to the fully expanded position when the spinal rod is fully reduced into the channel.

13. A method for aligning vertebral bodies of a spine comprising:
fastening a bone screw member of a spinal fixation device to a vertebral body, the spinal fixation device including:
a housing defining a longitudinal axis;
the bone screw member including a head and a threaded shaft, the head selectively securable within the housing;
a locking ring disposed within the housing, the locking ring biased in a neutral position and radially expandable to a partially expanded position when the head of the bone screw member is positioned therein, the partially expanded position retaining the head of the bone screw member within the housing; and
a crush ring disposed within the housing proximal to the locking ring and adjacent the head of the bone screw member, the crush ring having an initial state and a deformed state when a force is applied to the crush ring, the crush ring pushing against the head of the bone screw member when transitioning from the initial state to the deformed state which expands the locking ring to a fully expanded position to fix the bone screw member to the housing; and
positioning a portion of a spinal rod within a channel defined in the housing of the spinal fixation device.

14. The method of claim 13, further comprising:
rotating the housing with respect to the bone screw member; and
fully reducing the spinal rod into the channel.

15. The method of claim 14, wherein rotating the housing includes moving the housing within a cone of angulation of about 95° of the bone screw member relative to the longitudinal axis of the housing.

16. The method of claim 13, further including assembling the spinal fixation device prior to fastening the bone screw member to the vertebral body.

17. The method of claim 16, wherein assembling the spinal fixation device includes:
positioning the crush ring within the housing;
positioning the locking ring in the housing; and
inserting the head of the bone screw member into the housing and through the locking ring to couple the bone screw member to the housing.

* * * * *